United States Patent [19]

Morison

[11] 4,255,964

[45] Mar. 17, 1981

[54] FLUID MONITOR

[75] Inventor: Rodney Morison, Huntington Beach, Calif.

[73] Assignee: The Garrett Corporation, Los Angeles, Calif.

[21] Appl. No.: 965,369

[22] Filed: Nov. 30, 1978

[51] Int. Cl.³ .................... G01N 29/02; G06F 7/64
[52] U.S. Cl. .................................... 73/24; 364/496
[58] Field of Search ................................ 73/24, 597

[56] References Cited

U.S. PATENT DOCUMENTS

| | | | |
|---|---|---|---|
| 2,952,153 | 9/1960 | Robinson | 73/24 X |
| 3,374,659 | 3/1968 | Sanford et al. | 73/23.1 |
| 3,429,177 | 2/1969 | Webb | 73/24 |
| 3,468,157 | 9/1969 | Burk et al. | 73/24 |
| 3,789,655 | 2/1974 | Passeri | 73/24 |
| 3,981,176 | 9/1976 | Jacobs | 73/24 |
| 4,056,970 | 11/1977 | Sollish | 73/597 |
| 4,119,950 | 10/1978 | Redding | 73/24 X |
| 4,155,246 | 5/1979 | Dempster et al. | 73/24 |

FOREIGN PATENT DOCUMENTS

| | | | |
|---|---|---|---|
| 574819 | 1/1946 | United Kingdom | 73/24 |
| 727891 | 4/1955 | United Kingdom | 73/24 |

OTHER PUBLICATIONS

Publication: "Sonic Gas Analyzer for Measurement of $CO_2$ in Expired Air", S. D. Stott, (p. 914), vol. 28, No. 11, Nov. 1957, R. of Scient. Ins.

Primary Examiner—Daniel M. Yasich
Attorney, Agent, or Firm—Fay I. Konzem; J. Richard Konneker; Albert J. Miller

[57] ABSTRACT

A fluid monitor for determining the percent composition of a fluid mixture of unknown composition when compared to a reference fluid mixture of known composition.

6 Claims, 1 Drawing Figure

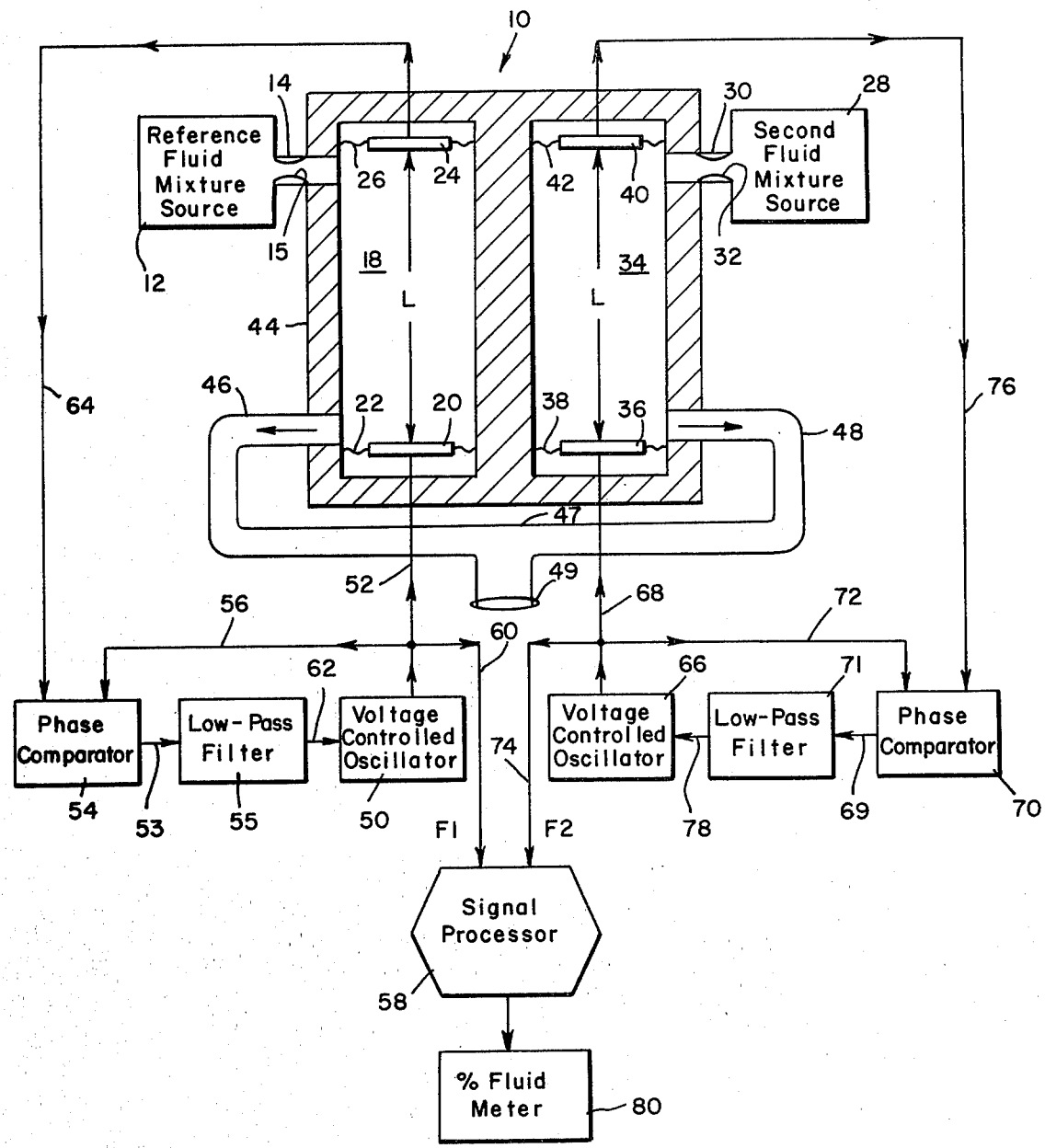

FLUID MONITOR

BACKGROUND OF THE INVENTION

Several methods have been previously used to determine the percent composition of a fluid mixture. One such method uses two acoustic chambers, one chamber containing a reference fluid mixture with a known percent composition, and the second chamber containing a fluid mixture whose percent composition is to be determined. A fixed frequency acoustic wave signal is sent through both chambers and the phase shift or differential is measured between the signals emanating from the two acoustic chambers. The composition of the fluid mixture is then determined by the phase differential between the signal passed through the reference fluid mixture and the signal passed through the fluid mixture of unknown composition.

This acoustic phase differential method of determining the composition of a fluid has several disadvantages. One such disadvantage is the limited accuracy imposed on phase differential measurements by the equipment used to make such measurements. For example, the phase differential in typical gaseous fluids may only be a few tens of degrees, which is difficult to measure with a great degree of accuracy. In certain environments, such as in an aircraft, it is imperative that a fluid monitor give very accurate measurement irrespective of temperature changes that can produce temperature differences between the fluids in the two acoustic chambers, thus introducing errors in the phase differential.

SUMMARY OF THE INVENTION

The fluid monitor, in accordance with the invention, includes apparatus for determining the resonant frequency of an acoustic chamber which is filled with a reference fluid mixture of known percent composition. The monitor further includes apparatus for determining the resonant frequency of another acoustic chamber which contains a fluid mixture of unknown percent composition. The fluid monitor also provides circuitry for comparing the resonant frequency of the chamber with the reference fluid mixture and the resonant frequency of the chamber with the fluid mixture to determine the percent composition of the fluid mixture.

One advantage of the present invention, which uses resonant frequencies to determine the percent composition of a fluid mixture, over the phase differential method is that resonant frequencies can be controlled and measured much more precisely and inexpensively than phase differentials can be measured.

BRIEF DESCRIPTION OF THE DRAWING

The single FIGURE is a partially sectional, partially schematic representation of the fluid monitor of the present invention.

DESCRIPTION OF THE PREFERRED EMBODIMENT

Referring now to the figure, the fluid monitor 10 is coupled to a reference fluid mixture source 12 by a conduit 14. A flow limiting valve 15 is used to avoid pressure buildup. The reference fluid mixture (of known percent composition) passes through the conduit 14 into an acoustic chamber 18 which contains an acoustic transmitting transducer 20 and an acoustic receiving transducer 24, such as a piezoelectric transducer. The transducers 20 and 24 are held in place in the chamber 18 by the perforated supports 22 and 26 respectively. The perforations permit the flow of reference fluid around the transducers 20 and 24. The transmitting transducer 20 sends a signal across the chamber 18 which is accepted by the receiving transducer 24. These transducers perform the functions of launching, receiving, and reflecting an acoustic wave front.

A second fluid mixture source 28, containing a fluid mixture of unknown percent composition is coupled to a second acoustic chamber 34 by a conduit 30. A flow limiting valve 32 is used to avoid pressure buildup in the acoustic chamber 34. The acoustic chamber 34 contains an acoustic transmitting transducer 36 and an acoustic receiving transducer 40, such as a piezoelectric transducer. The transducers 36 and 40 are held in place in the chamber 34 by the perforated supports 38 and 42 respectively.

The supports 22, 26, 38 and 42 provide acoustic vibration isolation of the transducers 20, 24, 36 and 40 from the walls of the chambers 18 and 34. The transmitting transducer 36 sends an acoustic signal across the chamber 34 which is accepted by the receiving transducer 40.

The transducer 20 is located a distance L from the transducer 24. The distance L is chosen as some integral multiple of the calculated half wave-length of the acoustic signal in the reference fluid mixture in the chamber 18. The transducer 36 is located the same distance L from the transducer 40 in the chamber 34.

The acoustic chambers 18 and 34 are formed by a housing 44. In the preferred embodiment the housing 44 is made of a material having high thermal conductivity to provide close thermal coupling between the chambers 18 and 34 thereby maintaining the fluids and transducers at the same temperature.

A fluid mixture of known percent composition is taken in by the reference fluid mixture source 12, flows through the chamber 18 and exits the chamber via a vent 46 through a conduit 47 to an outlet vent 49.

A fluid mixture of unknown percent composition is taken in by the second fluid mixture source 28, flows through the chamber 34 and exits the chamber via a vent 48 through the conduit 47 to the outlet vent 49. The vents 46 and 48 are coupled together by the conduit 47 to the common outlet vent 49, which exits into a discharge region that is maintained at a pressure lower than that in either chamber 18 or 34. Since the fluids from both chambers exit via a common vent 49, equal pressures are maintained in each of the two chambers over large pressure variations.

A first voltage controlled oscillator (VCO) 50 is connected by an electric lead 52 to the transmitting transducer 20, to a phase comparator 54 by a lead 56 and to a signal processor 58 by a lead 60. The VCO 50 produces a signal to be delivered to the transmitting transducer 20 which in turn generates an acoustic signal which travels across the chamber 18 and through the reference fluid to the receiving transducer 24. The signal from the receiving transducer 24 is delivered via a lead 64 to the phase comparator 54.

The phase comparator 54 compares the phase of the signal from the chamber 18 (on line 64) against the phase of the signal from the VCO 50 (on line 56). The output of the phase comparator 54 is then filtered by low-pass filter 55 and applied (via line 62) to the VCO 50. The voltage output by the phase comparator 54 is proportional to the difference in phase between its inputs. The DC voltage from the phase comparator 54 thereby changes the frequency of oscillation delivered from the VCO 50 on the leads 52, 56, and 60. Phase errors due to noise are filtered out by the low-pass filter 55.

A second VCO 66 is connected to the transmitting transducer 36 by a lead 68, to a phase comparator 70 by a lead 72 and to the signal processor 58 by a lead 74. The VCO 66 provides a signal to the transmitting transducer 36 which generates an acoustical signal which travels across the chamber 34 and through the second fluid from the second fluid mixture source 28 to the receiving transducer 40. The signal from the receiving transducer 40 is then delivered via a lead 76 to the phase comparator 70. The phase comparator 70 then compares the phase of the signal from the receiving transducer 40 via a lead 76 with the signal from the VCO 66 via the lead 72 and outputs a DC voltage via the lead 69 to a low-pass filter 71. The filtered signal is then delivered via a lead 78 to the VCO 66. The DC voltage representing the phase differential of the two signals input into phase comparator 70 changes the frequency of oscillation which is delivered from the VCO 66 via the leads 68, 72 and 74.

The signal processor 58 receives two signals, F1 and F2. Signal F1 on th lead 60 from the VCO 50 represents the frequency required to maintain resonance in the acoustic chamber 18 and F2 on the lead 74, the adjusted frequency from the VCO 66, represents the frequency required to maintain resonance in the acoustic chamber 34. The signal processor 58 compares the resonant frequencies of the chamber 18 containing the reference fluid with the resonant frequency of the chamber 34 containing the fluid mixture and calculates the percent composition of the fluid mixture from the second fluid source 28.

The signal processor 58 could be a commercially available micro-processor which could be programmed to convert the resonant frequency differential signals to the percent of a fluid in the fluid mixture flowing from second fluid source 28.

A percent fluid meter 80 receives the signal representing the percent of fluid which is desired to be measured in the fluid mixture and visually displays that information on the meter 80. Alternatively, the meter 80 gives off an audible signal when the amount present of a particular fluid in the chamber 34 reaches a certain percent.

OPERATION OF THE FLUID MONITOR

When the VCO 50 is activated to excite the transmitting transducer 20 at the fundamental resonant mode of the acoustic chamber 18, an acoustic pressure antinode is established at the receiving transducer 24 surface 180° out of phase with the antinode at the transmitting transducer 20. The output of the receiving transducer 24 delivers a signal on the lead 64 to the phase comparator 54. The phase comparator 54 senses whether this signal from the transducer 24 leads or lags the signal from the VCO 50. The output of the phase comparator 54 on the lead 53 is a DC signal having sense and magnitude to drive the VCO frequency toward the chamber resonant frequency condition. Therefore, the DC voltage from the phase comparator 54 causes the VCO 50 to maintain the resonant condition. At the resonant condition of the chamber 18, the two signals input to the phase comparator 54 (on the lead 56 and 64) are in phase and the resultant voltage to the VCO 50 on the lead 62 continually maintains the resonant condition. Thus, the system performs like a null-seeking system, avoiding the errors inherent in analog phase differential measurement.

The VCO 50, the low pass filter 55 and the phase comparator 54 form a phase locked loop. This phase locked loop automatically locks onto the frequency of the acoustic chamber 18 resonance which is determined by the sound velocity through the fluid in the chamber 18. More explicitly, the velocity V of sound waves propogated through a fluid is given by:

$$V = \left(\frac{\gamma RT}{M}\right)^{\frac{1}{2}} \tag{1}$$

Where $\gamma$ is the ratio of specific heats, R is the universal gas constant, T is the absolute temperature and M is the mean molecular weight of the fluid. The velocity of sound in a fluid determines the audio frequency at which a fluid-filled chamber with both ends closed resonates when an acoustic wave is transmitted back and forth along the axis of the chamber. With the transmitting transducer 20 radiating plane sound waves from one end of the chamber 18, the fundamental resonant frequency condition occurs when the sound wave length is twice the chamber length.

$$f = \left(\frac{V}{2L}\right) \cdot (n) \tag{2}$$

Where f is the frequency, L is the length of the chamber, and n = 1,2,3,4 identifies the fundamental and harmonic resonant modes. At these resonant mode frequencies, the acoustic signals received by the acoustic receiving transducer 24 located at the end of the chamber 18 opposite the transmitting transducer 20, reach maximums of amplitude. The received signals are 180° out of phase with the transmitting signals for resonances corresponding to odd values of n, and in phase for even values of n. It is this fixed phase relationship between transmitted and received audio signals that keeps the transmitting transducer 20 always excited at the mode of resonant frequency chosen for operation.

The specific frequency within a mode at which the chamber resonates is a function of the fluid density or molecular weight. Combining equations 1 and 2 gives the relationship between resonant frequency and the mean molecular weight of the fluid:

$$f(\text{resonance}) = \left(\frac{n}{2L}\right) \times \left(\frac{\gamma RT}{M}\right)^{\frac{1}{2}} \tag{3}$$

As the resonant condition of the chamber 18 shifts with changes in the content of the fluid in the chamber 18, the phase of the acoustic wave arising at the receiving transducer 24 also shifts. This acoustic signal phase shift leads or lags the 180° condition (or 0° condition if an even harmonic has been chosen) of the previous resonant condition. This also means that the signal from the receiving transducer 24 shifts phase with respect to the original driving frequency (on the lead 52) provided by VCO 50. The frequency output from the VCO 50 (on the lead 56) and the phase-shifted output from the receiving transducer 24 (on the lead 64) are both fed into the phase comparator 54. The difference in phase will create a change in DC voltage out of the phase comparator 54. The phase comparator output on the lead 53 is then fed through the low-pass filter 55 to the input to the VCO 50. The low-pass filter 55 provides stability to the phase locked loop and allows the loop gain to be large enough to achieve very close adherence to the acoustic resonance frequency with its corresponding 180° or 0° phasing conditions that occur across the acoustic chambers. This assures that the VCO frequency is determined by the acoustic chamber resonant condition. The low-pass filter also allows a high degree of immunity to acoustic noise. The voltage from the phase comparator 54 drives the frequency of the VCO 50 to the new resonant frequency of the acoustic chamber 18, whether higher or lower than the previous value.

The second phase locked loop consisting of the acoustic chamber 34, the VCO 66, the filter 71 and the phase comparator 70 functions in the same manner as the phase locked loop containing the acoustic chamber 18, just described.

The frequencies from the two chambers 18 and 34 will generate digital signals on which the signal processor 58 can operate. The signal processor 58 will perform the necessary arithmetic operations on the ratio of the two resonant frequencies to calculate the percent composition of the fluid mixture in the chamber 34.

An example of one possible use or implementation of the fluid monitor 10 of the present invention is in connection with an aircraft's oxygen-enriched air system which supplies oxygen-enriched breathing air to the aircraft crew and passengers. Also, an hypoxia warning system is needed to alert the crew when the oxygen partial pressure delivery to the cabin drops below the minimum physiologically required level. Applying the present invention to such a use, the chamber 18 is supplied with ambient air, which is used as a reference gas since ambient air always contains 20.9 percent oxygen. This reference gas, namely, the ambient air provides a reference for comparison with the enriched oxygen in the oxygen-enriched air mixture which is supplied to the chamber 34. The oxygen-enriched air is that air present in the cockpit and the passengers' cabin. Thus, the resonant frequency of the ambient air chamber 18 is used as a reference and the resonant frequency of the oxygen enriched air chamber 34 is related to the concentration of oxygen in the chamber 34. The ratio of the two frequencies can then be processed by the signal processor 58, which calculates the percent of oxygen in the aircraft cabin and cockpit. Finally, the measurement of the total cockpit and cabin pressure is made by a pressure transducer. The signal processor then multiplies the signal from the pressure transducer representing the cabin pressure by the percent oxygen content obtained from comparing the resonant frequency of the ambient air with that of the oxygen enriched air mixture, yielding the oxygen partial pressure. When the oxygen partial pressure is less than a predetermined value, a relay closes, thereby sending a signal to a warning light, warning the airplane crew of the unacceptably low oxygen partial pressure level.

The fluid monitor of the present invention very accurately measures the percent composition of a fluid mixture over a wide range of pressure and temperature changes by using a phase locked loop configuration, which sustains resonance of the acoustic chambers 18 (containing the reference fluid) and the chamber 34 (containing the fluid mixture) regardless of the changes in pressure or temperature. Then by comparing the resonant frequencies of these two resonant frequencies, the percent composition of the fluid mixture can precisely and inexpensively be measured.

While specific embodiments of the invention have been illustrated and described, it is to be understood that these embodiments are provided by way of example only and the invention is not to be construed as being limited thereto, but only by the proper scope of the following claims:

What is claimed is:

1. A fluid monitor for monitoring the percent composition of a fluid mixture, said monitor comprising:
    a first acoustic chamber having a measurable resonant frequency and containing a reference fluid of known percent composition;
    a second acoustic chamber having a measurable resonant frequency and containing a fluid mixture of unknown percent composition;
    means for measuring the resonant frequency of said acoustic chambers, said measuring means including;
    a first phase locked loop comprising said first acoustic chamber coupled between a voltage controlled oscillator and a phase comparator, said phase comparator being coupled to said voltage controlled oscillator;
    a second phase locked loop comprising said second acoustic chamber coupled between a voltage controlled oscillator and a phase comparator, said phase comparator being coupled to said voltage controlled oscillator;
    a first transmitting transducer located in said first chamber for sending sound waves through the reference fluid;
    a second transmitting transducer located in said second chamber for sending sound waves through the fluid mixture;
    said first and second transmitting transducer being driven by a signal from said voltage controlled oscillator;
    a first receiving transducer located in said first chamber a predetermined distance from said transmitting transducer for accepting the sound waves and for converting the sound waves into a signal indicative of the reference fluid; and
    a second receiving transducer located in said second chamber a predetermined distance from said second transmitting transducer for accepting the sound waves and for converting the sound eaves into a signal indicative of the fluid mixture; and
    means for comparing the two resonant frequencies, said comparing means including;
    signal processor means coupled to said first and second phase locked loops for comparing the resonant frequency of the reference fluid in said first acoustic chamber with the resonant frequency of the fluid mixture in said second acoustic chamber and determining the percent composition of the fluid mixture.

2. The method of monitoring the percent composition of a fluid mixture comprising the steps of:
    (a) providing a first acoustic chamber having mounted therein first and second transducers spaced apart by a predetermined distance;
    (b) connecting to said first and second transducers a first phase locked electrical loop adapted to generate between said first and second transducers an acoustic signal having a frequency equal to a resonant frequency of said first acoustic chamber when it contains a reference fluid of known percent composition;

(c) introducing into said first acoustic chamber a reference fluid of known percent composition;

(d) providing a second acoustic chamber having mounted therein third and fourth transducers spaced apart by a predetermined distance;

(e) connecting to said third and fourth transducers a second phase locked electrical loop adapted to generate between said third and fourth transducers an acoustic signal having a frequency equal to a resonant frequency of said second acoustic chamber when it contains a fluid mixture of unknown percent composition;

(f) introducing into said second acoustic chamber a fluid mixture of unknown percent composition;

(g) energizing said first and second phase locked loops; and (h) determining by direct frequency comparison the difference between the frequencies of the acoustic signals to thereby determine the percent composition of the fluid mixture.

3. The method of claim 2 wherein said connecting step (b) is performed by providing a first voltage controlled oscillator having an input and an output, providing a first phase comparator having an output and a pair of inputs, connecting said output of said first voltage controlled oscillator to said first transducer and to one of said inputs of said first phase comparator, connecting said output of said first phase comparator to said input of said first voltage controlled oscillator, and connecting the other of said inputs of said first phase comparator to said second transducer, and wherein said connecting step (e) is performed by providing a second voltage controlled oscillator having an input and an output, providing a second phase comparator having an output and a pair of inputs, connecting said output of said second voltage controlled oscillator to said third transducer and to one of said inputs of said second phase comparator, connecting said output of said second phase comparator to said input of said second voltage controlled oscillator, and connecting the other of said inputs of said second phase comparator to said fourth transducer.

4. The method of claim 3 wherein said determining step (h) is performed by providing a signal processor having an output and a pair of inputs, connecting one of said signal processor inputs to said output of said first voltage controlled oscillator, connecting the other of said signal processor inputs to said output of said second voltage controlled oscillator, and connecting to said signal processor output means for receiving a signal therefrom and utilizing said signal to indicate the percent composition of the fluid mixture introduced into said second acoustic chamber.

5. A fluid monitor for monitoring the percent composition of a fluid mixture, said fluid monitor comprising:

(a) a first acoustic chamber adapted to receive a reference fluid of known percent composition and, when containing the reference fluid, having a measurable resonant frequency;

(b) a second acoustic chamber adapted to receive a fluid mixture of unknown percent composition and, when containing the fluid mixture, having a measurable resonant frequency;

(c) means, including first phase locked loop means associated with said first acoustic chamber, for electrically generating sound waves within said first acoustic chamber having a frequency equal to said first acoustic chamber resonant frequency, said sound wave-generating means (c) further including first transmitting transducer means connected to said first phase locked loop means and located in said first chamber for sending sound waves through the reference fluid, and first receiving transducer means located in said first chamber a predetermined distance from said first transmitting transducer means and connected to said first phase locked loop means for accepting sound waves generated through the reference fluid by said first transmitting transducer means and for converting such sound waves into a signal indicative of the reference fluid, said first phase locked loop means including a first voltage controlled oscillator having an output connected to said first transmitting transducer means, and a first phase comparator interconnected between said first receiving transducer means and said first volage controlled oscillator;

(d) means, including second phase locked loop means associated with said second acoustic chamber, for electrically generating sound waves within said second acoustic chamber having a frequency equal to said second acoustic chamber resonant frequency, said sound wave-generating means (d) further including second transmitting transducer means connected to said second phase locked loop means and located in said second chamber for sending sound waves through the fluid mixture, and second receiving transducer means located in said second chamber a predetermined distance from said second transmitting transducer means and connected to said second phase locked loop means for accepting sound waves generated through the fluid mixture by said second transmitting transducer means and for converting such sound waves into a signal indicative of the fluid mixture, said second phase locked loop means including a second voltage controlled oscillator having an output connected to said second transmitting transducer means, and a second phase comparator interconnected between said second receiving transducer means and said second voltage controlled oscillator; and (e) signal processing means connected between said outputs of said first and second voltage controlled oscillators for measuring and directly comparing the frequencies of said sound waves electrically generated within said first and second acoustic chambers to determine the percent composition of the fluid mixture in said second chamber.

6. Fluid monitoring apparatus for monitoring the percent composition of a fluid mixture, said apparatus comprising:

(a) a housing;

(b) first and second acoustic chambers formed within said housing, each of said first and second acoustic chambers having a pair of opposite ends and a measurable resonant frequency;

said first acoustic chamber having first and second transducers mounted therein on perforated supports positionned adjacent its opposite ends and spaced apart by a predetermined distance, said first acoustic chamber containing a reference fluid;

said second acoustic chamber having first and second transducers mounted therein on perforated supports positioned adjacent its opposite ends and spaced apart by a predetermined distance, said second acoustic chamber containing a fluid mixture;

(c) a first voltage controlled oscillator having an input and an output, said first oscillator for producing and passing a signal to said first transducer in said first chamber to generate an acoustical signal therefrom which will travel across said first chamber, through the reference fluid, and be received by said second transducer in said first chamber;

(d) a first phase comparator having a first and second input and an output, for determining the phase differential between its input signals, said first input of said first phase comparator being connected to said second transducer in said first chamber and said second input of said first phase comparator being connected to said output from said first voltage controlled oscillator, said output of said first phase comparator being connected to said input of said first voltage controlled oscillator;

(e) a second voltage controlled oscillator having an input and an output, said second oscillator for producing and passing a signal to said first transducer in said second chamber to generate an acoustical signal therefrom which will travel across said second chamber through the fluid mixture, and be received by said second transducer in said second chamber;

(f) a second phase comparator having a first and second input and an output, for determining the phase differential between its input signals, said first input of said second phase comparator being connected to said second transducer in said second chamber and the second input of said second phase comparator being connected to said output from said second voltage controlled oscillator, said output of said second phase comparator being connected to said input of said second voltage controller oscillator; and (g) signal processing means having a first and second input, said first input of said signal processing means being connected to said output of said first oscillator and said second input of said signal processing means being connected to said output of said second oscillator, said signal processing means for comparing the resonant frequency of said first acoustic chamber containing the reference fluid with the resonant frequency of said second acoustic chamber containing the fluid mixture and calculating the percent composition of the fluid mixture.

* * * * *